United States Patent [19]

Grifka

[11] Patent Number: 5,376,068
[45] Date of Patent: Dec. 27, 1994

[54] ANKLE JOINT BRACE

[75] Inventor: Joachim Grifka, Bochum, Germany

[73] Assignee: Otto Bock Orthopaedische Industrie Besitz- und Verwaltungs KG, Duderstadt, Germany

[21] Appl. No.: 55,019

[22] Filed: Apr. 30, 1993

[30] Foreign Application Priority Data

Apr. 30, 1992 [DE] Germany .............................. 9205791

[51] Int. Cl.⁵ ............................ A61F 3/00; A61F 5/00
[52] U.S. Cl. ........................................ 602/27; 602/208
[58] Field of Search ................... 602/5, 23, 24, 27, 28, 602/29

[56] References Cited

U.S. PATENT DOCUMENTS

| | | | |
|---|---|---|---|
| 3,804,085 | 4/1974 | Eshuis et al. | 602/28 |
| 3,916,886 | 11/1975 | Rogers | 602/28 |
| 3,976,059 | 8/1976 | Lonardo | 602/28 |
| 3,988,501 | 10/1976 | Schad | 602/28 |
| 3,989,041 | 11/1976 | Davies . | |
| 4,289,122 | 9/1981 | Mason et al. | 602/27 |
| 4,554,912 | 11/1985 | Haberman | 602/27 |
| 4,566,447 | 1/1986 | Deis | 602/28 |
| 4,998,537 | 3/1991 | Rau | 602/27 |
| 5,022,390 | 6/1991 | Whiteside . | |
| 5,121,742 | 6/1992 | Engen | 602/16 |
| 5,257,969 | 11/1993 | Mance | 602/28 |

FOREIGN PATENT DOCUMENTS

| | | |
|---|---|---|
| 2354087 | 2/1978 | France . |
| 2259945 | 6/1974 | Germany . |
| 2808968 | 5/1981 | Germany . |
| 607614 | 9/1978 | Switzerland . |

Primary Examiner—Richard J. Apley
Assistant Examiner—Beverly A. Meindl
Attorney, Agent, or Firm—Foley & Lardner

[57] ABSTRACT

An ankle joint brace with a dorsal leg shell extending over the back of the foot, which can be fastened by strappings or similar devices to the calf. In order to improve the function and the structure of this ankle joint brace, the leg shell is extended by a frontal shell section underneath the sole of the foot and, in the area of the ankle joint outer ligaments, it is taken inward and tapered sharply toward the back, creating a cut-out, and an elastic rubber tensioning strap holds the leg shell with a dynamic pull, underneath and outward on the frontal shell section on one side and inward and above in the calf area on the other side, the leg shell being flexible in dorsal extension and pronation because of its shape, while the tensioning strap restricts supination and plantar flexion.

7 Claims, 2 Drawing Sheets

ANKLE JOINT BRACE

BACKGROUND OF THE INVENTION

The invention relates to an ankle joint brace with a dorsal leg shell extending over the back of the foot, which can be fastened to the calf by means of strapping or something similar.

Until a few years ago, the conservative treatment provided for newly-caused lesions of the outer ligaments of the ankle joint was, first of all, to immobilize the foot, pronated and dorsally extended, in a plaster cast for about two weeks until the swelling had largely subsided and then place it in a lower-leg walking cast for a subsequent period of about four weeks. For various reasons, a plaster treatment of this type is generally considered today to be obsolete. Thus, conservative care today is oriented toward functional treatment.

Ankle joint braces available to date almost exclusively surround the back of the foot, without extending farther toward the sole of the foot. Solid splint components or strappings are anchored on the damaged outer area of the ankle joint, swollen by blood flow and lymphatic fluid, which can irritate this sensitive region. However, the principal problem is that plantar flexion is usually not restricted. When shoes are equipped with ankle joint supports, the person in question generally causes plantar flexion of the foot when inserting it into the shoe, and thereby damages the ligaments in the process of being healed, especially the talo-figulare anterius ligament.

The tape dressing has proven its value in a functional sense. It does indeed achieve firm support; on the other hand, it has the disadvantage of the time and material required to bind the dressing. Other disadvantages result from the need to repeatedly replace the tapes, from a hygienic point of view and from the necessity that the placement of the tapes requires not only a great deal of time, but especially sufficient experience as well.

SUMMARY OF THE INVENTION

The invention has the purpose of improving the function and the construction of the ankle joint brace described at the beginning.

This purpose is achieved in accordance with the invention in that a section of the leg shell extends forward, underneath the sole of the foot and is sharply tapered in the area of the outer ligaments of the ankle joint by a cut-out which leaves the area free and that an elastic rubber tensioning strap grips the leg shell with a dynamic pull, holding the outside and bottom of the forward foot section of the shell on one side and the inside and the top in the calf area; the leg shell is bendable in dorsal extension and pronation, while the tensioning strap restricts supination and plantar flexion.

To achieve the object and in accordance with the purpose of the invention, as embodied and broadly described herein, an ankle joint brace comprises a dorsal leg shell having a shape for extending over a back of a foot, which leg shell is adapted to be fastened by strappings or similar devices to a calf; a frontal shell section extending from the leg shell underneath a sole of the foot; and an elastic rubber tensioning strap for holding the leg shell with a dynamic pull, underneath and outward on the frontal shell section on one side and inward and above in a calf area on another side, and for restricting supination and plantar flexion; wherein the leg shell is flexible in dorsal extension and pronation because of its shape; and wherein, in an area of the ankle joint outer ligaments, the leg shell is taken inward and tapered sharply toward the back, creating a cut-out portion.

This ankle joint brace in accordance with the invention meets the requirements of conservative functional treatment, for it permits free movement of the foot in dorsal extension and pronation, while plantar flexion and pronation are increasingly restricted as the extent of movement increases, as a result of the dynamic pull exerted by the tensioning strap. The area of the outer ligaments of the ankle is completely spared.

It is particularly easy to put on the brace. The tensioning strap can also be used to wrap around the front of the foot to fix it in place. The only other components needed for fastening are an instep strap and a calf band, which are easy to fit and fasten with hook and loop fastenings such as a Velcro fastening.

In order to permit it to be unrolled over the metatarsal heads, it is advantageous if the section of the shell extending to the front of the foot leaves the first metatarsal head free even when it covers the sole of the foot as far as the bottom of the front of the foot.

While previously known embodiments kept the foot fixed in a specific position, by means of a half-shell-shaped leg shell holding the calf and the foot on both sides to the sole of the foot, for example, the structure of the solution in accordance with the invention operates dynamically, and gives rise to a constant pull in the direction of the therapeutic position when the foot is relaxed. In this way, the ideal position is ensured for the foot of an athlete who is in an unconscious condition,- while the greatest possible freedom is ensured for the practice of athletic activity.

Other characteristics and objects of the invention will be described in greater detail in connection with further advantages of the invention, on the basis of an explanatory example.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate a presently preferred embodiment of the invention, and, together with the general description give above and the detailed description of the preferred embodiment given below, serve to explain the principles of the invention.

The figures show an embodiment of the invention used as an example.

DETAILED DESCRIPTION OF THE PREFERRED EMBODIMENTS

Figure 1:
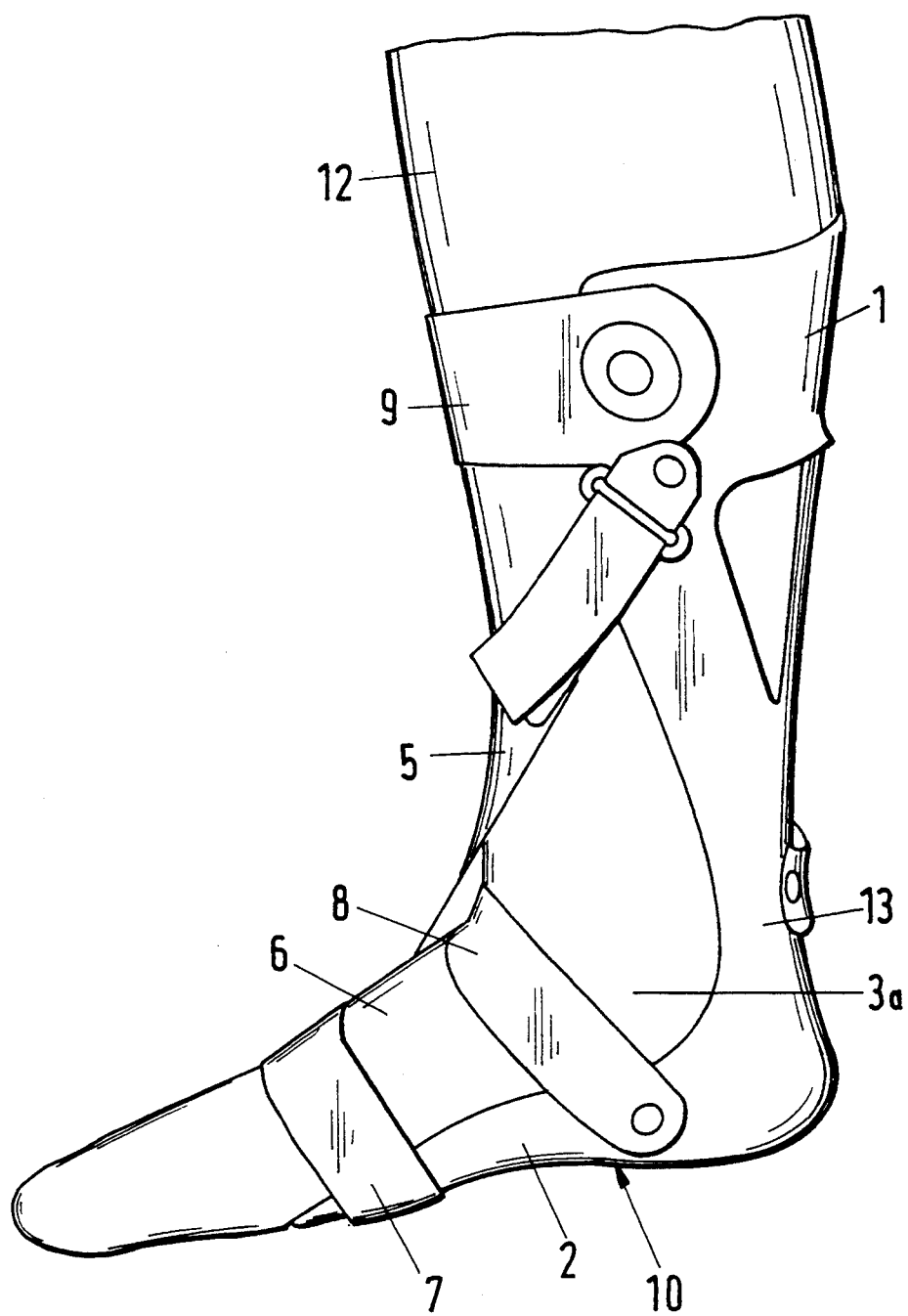
FIG. 1 shows an inside view of a ankle joint brace fastened to the calf and/or the foot.
Figure 2:
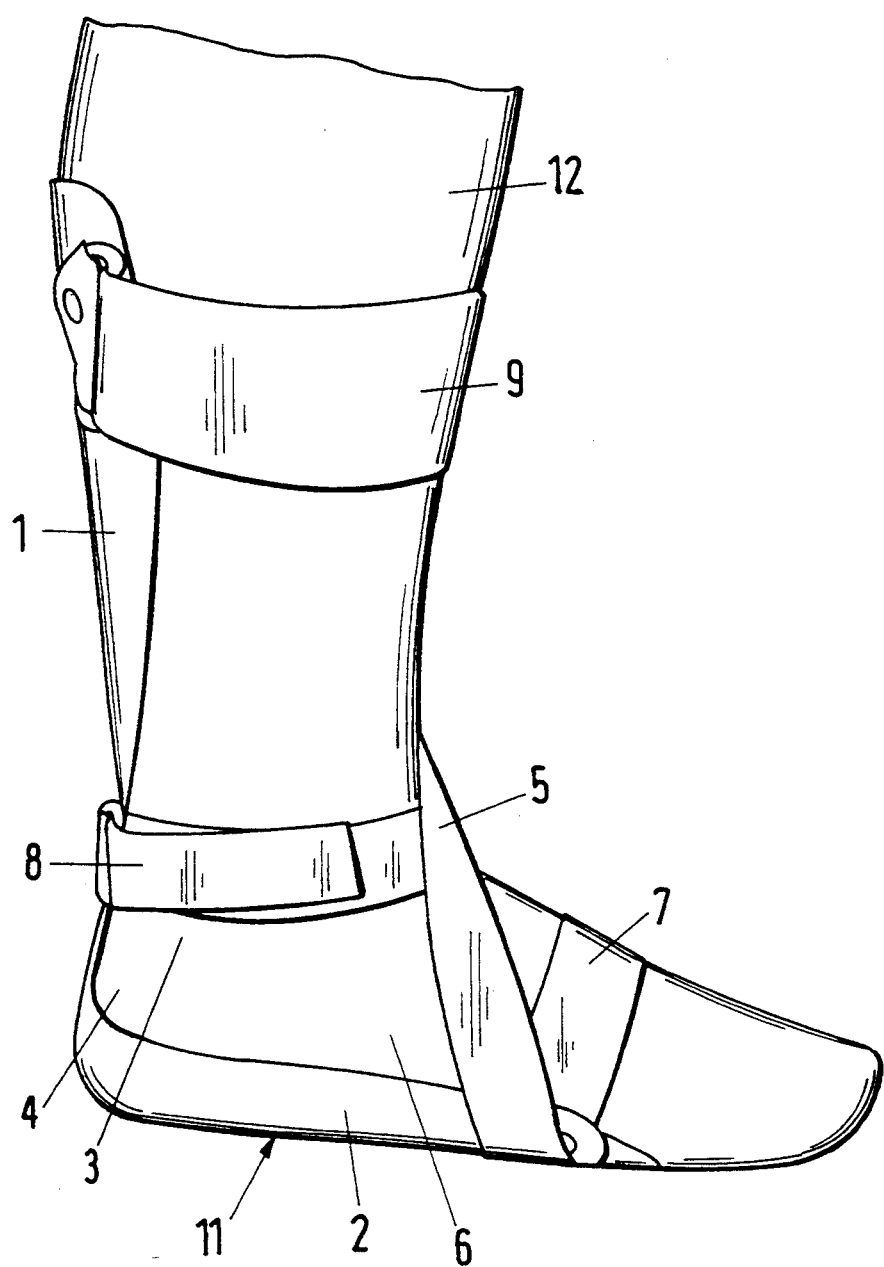
FIG. 2 shows an outside view of the illustration in accordance with FIG. 1.

The ankle joint brace illustrated in FIGS. 1 and 2 exhibits a dorsal leg shell 1 extending over the back of the foot which extends into a frontal shell section 2 underneath the sole of the foot and which is taken inward in an inner ligament area 3a of the ankle joint and tapered sharply in a direction from calf to heel, creating a cutout 4 which leaves the outer ligament area 3 of the ankle joint free. The ankle joint brace in accordance with the invention also includes an elastic rubber tensioning strap 5, which holds the leg shell 1 with a dynamic pull, underneath and outward on the frontal shell section 2 on one side and inward and above in the calf area on the other side. The tensioning strap 5 thus runs in a ventral diagonal. The leg shell 1 is flexible in dorsal extension and pronation because of its shape, while the tensioning strap 5 restricts supination and plantar flexion.

In the embodiment illustrated, the tensioning strap 5 simultaneously serves as a strap or band 7 to hold the front of the foot 6 in place, that is, immobile. The ankle joint brace can be further fastened by an instep strap 8 and a calf band 9 which can both be secured by a Velcro or similar type of fastener.

In FIG. 1, the arrow 10 indicates the inner edge of the foot, while in FIG. 2 the arrow 11 points to the outer edge of the foot. A comparison of FIGS. 1 and 2 makes it clear that the leg shell 1 holds the calf 12 only on the dorsal and inner sides, and that the outer side of the calf 12 is left mainly free. Because of the large cut-out 4 designed in the area of the ankle joint outer ligament 3, a relatively narrowly-constructed shell connecting strip 13 is formed, lying mainly on the inner side of the foot, which bends elastically and gives the leg shell 1 inherent tension.

The leg shell I is composed preferably of a thermoplastic synthetic and it can therefore be post-formed and individually fitted as a result. It can be worn inside a shoe.

Additional advantages and modifications will readily occur to those skilled in the art. Therefore, the invention in its broader aspects is not limited to the specific details, and representative devices, shown and described herein. Accordingly, various modifications may be made without departing from the spirit or scope of the general inventive concept as defined by the appended claims and their equivalents.

What is claimed is:

1. An ankle joint brace comprising:
   a dorsal leg shell having a shape for extending over a back of a foot, which leg shell is adapted to be fastened by strappings or similar devices to a calf;
   a frontal shell section extending from the leg shell underneath a sole of the foot; and
   an elastic rubber tensioning strap for exerting a dynamic pull, outward on the frontal shell section and inward and above in a calf area, and for restricting supination and plantar flexion;
   wherein the leg shell is flexible in dorsal extension and pronation because its shape
   is defined by a dorsal shell section taken inward in an inner ligament area of the ankle joint with a width which tapers sharply in a direction from calf to heel, creating a cut-out portion which leaves the outer ligament area of the ankle joint free.

2. An ankle joint brace in accordance with claim 1, wherein the tensioning strap includes a band for simultaneously wrapping around the foot to hold a front of the foot immobile.

3. An ankle joint brace comprising:
   a dorsal leg having a shape for extending over a back of a foot, which leg shell is adapted to be fastened by strappings or similar devices to a calf;
   a frontal shell section extending from the leg shell underneath a sole of the foot; and
   an elastic rubber tensioning strap for exerting a dynamic pull, outward on the frontal shell section and inward and above in a calf area and for restricting supination and plantar flexion;
   wherein the leg shell is flexible in dorsal extension and pronation; and
   wherein in an area of the ankle joint outer ligaments, the leg shell has a width which tapers sharply in a direction from calf to the heel, creating a cut-out portion;
   wherein the tension in strap includes a band for simultaneously wrapping around the the foot to hold a front of the foot immobile; and
   wherein, aside from the band holding the front of the foot, said strappings or similar devices include only an instep strap and a calf band.

4. An ankle joint brace in accordance with claim 1, wherein the frontal shell section leaves a first metatarsal bone free under the front of the foot, even though it covers the sole of the foot to the front.

5. An ankle joint brace in accordance with claim 2, wherein the frontal shell section leaves a first metatarsal bone free under the front of the foot, even though it covers the sole of the foot to the front.

6. An ankle joint brace in accordance with claim 3, wherein the frontal shell section leaves a first metatarsal bone free under the front of the foot, even though it covers the sole of the foot to the front.

7. An ankle joint brace in accordance with claim 1, wherein said tensioning strap exerts a constant pull in a direction of a therapeutic position at times when a wearer's foot is relaxed.

* * * * *